United States Patent
Rabasco et al.

(10) Patent No.: US 7,427,444 B2
(45) Date of Patent: *Sep. 23, 2008

(54) POLYMER EMULSION COATINGS FOR CELLULOSIC SUBSTRATES WITH IMPROVED BARRIER PROPERTIES

(75) Inventors: John Joseph Rabasco, Allentown, PA (US); Ronald Bernal Jones, Allentown, PA (US); Christian Leonard Daniels, Macungie, PA (US); Richard Henry Bott, Macungie, PA (US); John Joseph Halat, Breinigsville, PA (US)

(73) Assignee: Air Products Polymers, L.P.

( * ) Notice: Subject to any disclaimer, the term of this patent is extended or adjusted under 35 U.S.C. 154(b) by 35 days.

This patent is subject to a terminal disclaimer.

(21) Appl. No.: 10/620,654

(22) Filed: Jul. 16, 2003

(65) Prior Publication Data

US 2005/0014013 A1 Jan. 20, 2005

(51) Int. Cl.
*B32B 23/04* (2006.01)
(52) U.S. Cl. ...................... 428/511; 428/510
(58) Field of Classification Search ........... 428/510, 428/511
See application file for complete search history.

(56) References Cited

U.S. PATENT DOCUMENTS

| | | | |
|---|---|---|---|
| 3,226,352 A | 12/1965 | Helin et al. ............. 260/29.6 |
| 3,355,322 A | 11/1967 | Shepherd et al. | |
| 3,436,363 A | 4/1969 | Helin .................. 260/29.6 |
| 3,692,723 A | 9/1972 | Kasagi et al. ......... 260/29.6 E |
| 4,128,518 A | 12/1978 | Oyamada et al. .... 260/29.6 WB |
| 4,503,185 A * | 3/1985 | Hausman et al. ........... 524/553 |
| 4,599,378 A * | 7/1986 | Hausman et al. ........... 524/554 |
| 5,539,035 A | 7/1996 | Fuller et al. ............... 524/322 |
| 5,700,516 A | 12/1997 | Sandvick et al. ........... 427/155 |
| 5,747,578 A | 5/1998 | Schmitz et al. ............ 524/502 |
| 5,763,100 A | 6/1998 | Quick et al. ............... 428/486 |
| 5,872,181 A * | 2/1999 | Daniels et al. ............. 524/563 |
| 5,876,815 A | 3/1999 | Sandstrom et al. ......... 428/36.8 |
| 5,897,411 A | 4/1999 | Stark et al. ................. 428/511 |
| 5,989,724 A | 11/1999 | Wittosch et al. ............ 428/511 |
| 6,063,858 A * | 5/2000 | Daniels et al. ............. 524/563 |
| 6,066,379 A | 5/2000 | Ma et al. .................... 428/53 |
| 6,319,978 B1 * | 11/2001 | Daniels et al. ............. 524/564 |
| 6,548,120 B1 | 4/2003 | Wittosch et al. | |
| 6,559,259 B2 * | 5/2003 | Kohlhammer et al. ....... 526/287 |
| 2004/0175589 A1* | 9/2004 | Rabasco et al. ............. 428/511 |
| 2004/0241475 A1 | 12/2004 | Morabito | |

FOREIGN PATENT DOCUMENTS

| | | | |
|---|---|---|---|
| CN | 1205341 A | | 1/1999 |
| EP | 0 890 625 | * | 1/1999 |
| EP | 0 990 688 | * | 4/2000 |
| EP | 1 454 930 | | 9/2004 |
| GB | 1 148 148 | | 4/1969 |
| JP | 4933353 B | | 9/1974 |
| JP | 02322216 | | 11/2002 |
| WO | 0214426 | | 2/2002 |
| WO | 0242342 | | 5/2002 |
| WO | 02079270 | | 10/2002 |

* cited by examiner

*Primary Examiner*—D. Lawrence Tarzano
*Assistant Examiner*—John D. Freeman

(57) ABSTRACT

A cellulosic product such as paper coating composition is disclosed comprising aqueous-based semi-crystalline vinyl acetate-ethylene polymer emulsions, containing crystalline ethylene segments, which are useful for imparting oil, grease, solvent, water, and moisture vapor resistance. The polymer emulsions are prepared via the direct aqueous-based free radical emulsion polymerization of ethylene with various other comonomers. The semi-crystalline aqueous-based polymer emulsions of this invention have a crystalline melting point and a crystalline heat of fusion ranging from 5 to 100 J/g. The semi-crystalline aqueous-based emulsion polymers of this invention can be used directly as a paper or paperboard coating for imparting oil, grease, solvent, water, and moisture vapor resistance. Further, the present invention provides a repulpable paper and paperboard.

18 Claims, No Drawings

POLYMER EMULSION COATINGS FOR CELLULOSIC SUBSTRATES WITH IMPROVED BARRIER PROPERTIES

BACKGROUND OF THE INVENTION

It is well known in the art that cellulosic products such as untreated paper are permeable to water and other aqueous and non-aqueous liquids. Thus, it has been common practice to coat or treat paper and other cellulosic products with various coatings, such as waxes, polymers, fluorocarbons and the like in order to impart barrier properties and resistance to various liquids, such as water, oil, grease, solvents, etc. Such coated or treated paper, paperboard and boxboard substrates are used for food packaging and food wrappers, food containers, and various other paper substrates that contact foods. Recent cellulosic substrate grade developments for packaging or holding high fat/oil content foods, such as fast food and microwave applications, require the coating on the cellulosic substrate to prevent fluids, such as hot oils and/or fats, from penetrating through the cellulosic substrate and staining the outside of the package. Further, such coatings must also prevent such fluid penetration through the cellulosic substrates for the shelf life of the packaged foods, which can experience elevated temperatures in warehouses and/or shipping vessels.

Water repellant paper products, such as paperboard for use in packaging meats, fruits and vegetables, coated with polyethylene and waxes are difficult to repulp. The coatings tend to hold the fibers together. Often the particles of the coatings stick to paper mailing equipment, wire presses, and dryers. In addition, many of the barrier coated paper products for packing food products and the like become tacky causing stacked or contiguous sheets of coated board to block or stick together.

Cellulosic substrates utilized for food packaging, such as fast food and microwave applications, need to be flexible since the material is often folded, scored or wrapped during conversion into the final container. Barrier coatings for these cellulosic substrates need to protect the cellulose fibers at these folds, scores or wraps to prevent wicking of oils, fats and other liquids through the substrate. Fluorocarbons accomplish this by lowering the surface energy of the fibers. Most polymer emulsion coatings fail to protect the fold or scoreline because the polymer films break when subjected to such stresses. The polymer emulsion coatings of this invention are unique in that their flexibility allows the coating to stretch over the fold or scoreline and prevent liquids from wicking through the substrate.

Representative patents illustrating the prior art in the field of barrier coated paper products include the following:

U.S. Pat. No. 5,897,411 discloses paper and paperboard for use in packaging operations, e.g., food packaging which have been coated with a repulpable moisture vapor barrier layer comprising a resin latex and a hydrophobic component with a platelet structure. Examples include polystyrene, styrene-acrylonitrile, carboxylated butadiene-styrene, ethylene/vinyl chloride and the like. Examples of hydrophobic components with a platelet structure include mica, talc, silica, etc.

U.S. Pat. No. 6,066,379 discloses a repulpable water repellant paperboard incorporating an aqueous coating containing a polymer matrix/wax/pigment mixture as a barrier as an improvement to wax-coated board. The water-repellant coating of film includes pigments, wax, and a polymer matrix of polymer chains ionically cross-linked through pendent carboxylic acid, such as carboxylated butadiene-styrene latexes.

U.S. Pat. No. 5,876,815 discloses a laminate product having both improved grease, oil, wax and solvent repellency and improved glueability and printability properties. The laminate comprises a paper substrate, i.e., the top side of at least one layer of a fluorine containing polymer moiety on at least one surface of the substrate and at least one layer comprising a latex on the at least one layer of a fluorine containing polymer moiety layer. Examples of latexes include styrene-acrylic copolymers, ethylene/vinyl acetate (Airflex 100HS), ethylene/vinyl chloride, vinyl acetate/acrylic etc.

WO 02/14426 A1 discloses grease resistant paper products incorporating a barrier formulation that does not contain fluorochemicals. The formulation is also useful as a coating or treatment for providing release properties to an underlying substrate without the use of silicone. The formulation contains polyvinyl alcohol and a fatty acid melamine and paraffin wax.

U.S. Pat. No. 5,989,724 discloses a recyclable and repulpable coated paper stock coated on one surface with a base coat and at least one additional coat over the base coat. Both coats are based upon polymers such as acrylic, ethylene-vinyl acetate, polyvinyl acetate, and the like. Unlike polyethylene films and wax coatings, the coatings described are repulpable.

U.S. Pat. No. 3,436,363 discloses a batchwise and a continuous process for the polymerization of ethylene in the presence of a polymerizable ethenoid unsaturated mono or polybasic carboxylic acid or sulfonic acid and water. Representative polymerizable ethenoid acids include acrylic, methacrylic, crotonic, itaconic, and the like. The solids level of the polymer emulsions is about 25 to 30% by weight. The emulsions are reported to be useful in paper coating, textile finishing, polishes, and surface coatings.

BRIEF SUMMARY OF THE INVENTION

This invention is directed to an improvement in cellulosic products, such as, paper or paperboard products having a barrier coating applied thereto which imparts a barrier against moisture vapor, oil, grease, solvent, water and other aqueous and non-aqueous fluids. The improvement resides in an emulsion polymerized ethylene-vinyl acetate polymer as said coating, said polymer having:

(a) a crystalline melting point ($T_m$) ranging from 35 to 110° C., preferably 50 to 90° C.; measured at a heat rate of 20° C./minute; and, (b) a tensile storage modulus of at least $1 \times 10^5$ dynes/cm$^2$ at 115° C. measured at 6.28 rad/sec.

In addition, these polymers should have (c) a crystalline heat of fusion ($H_f$) ranging from 5 to 100 joules per gram (J/g), preferably 15 to 70 J/g; (d) a glass transition temperature ($T_g$) of +25° C. to about −35° C., and (e) non-blocking at temperatures of about 50° C.

Significant advantages can be achieved with this invention and these include:

an ability to provide a direct method of preparing barrier-coating cellulosic containing compositions that do not require fluorochemicals;

an ability to produce paper and paperboard products that are microwavable and resistant to hot oils and greases;

an ability to employ a wet coating process to prepare paper and paperboard with barrier properties; and, an ability to provide for paperboard products that are repulpable unlike polyethylene paper and paperboard which are not repulpable and must be land filled.

DETAILED DESCRIPTION OF THE INVENTION

The aqueous based ethylene-vinyl acetate polymer emulsions of this invention are based upon vinyl acetate and ethylene with the level of polymerized units of vinyl acetate ranging from 15 to 90% by weight of the polymer and the level of polymerized units of ethylene ranging from 10% to 85% by weight; preferably from 25 to 80 weight percent vinyl acetate and 20 to 75% by weight ethylene; and most preferably from 35 to 75% by weight vinyl acetate and 25 to 65% by weight ethylene. Another embodiment of this invention is aqueous based vinyl acetate-ethylene polymer emulsions in which the polymer is comprised of 30 to 50 wt % vinyl acetate and 50 to 70 wt % ethylene.

An additional component for consistently enhancing the barrier properties of vinyl acetate-ethylene polymers is in the incorporation of a carboxylic acid or self-crosslinking component. Carboxylic acids include $C_3$-$C_{10}$ alkenoic acids, such as acrylic acid, methacrylic acid, crotonic acid, and isocrotonic acid, and alpha, beta-unsaturated $C_4$-$C_{10}$ alkenedioic acids such as maleic acid, fumaric acid, and itaconic acid. Crosslinking monomers include N-methylolacrylamide (NMA), a mixture of NMA and acrylamide, typically in a 50/50 ratio, often referred to as MAMD; acrylamidobutyraldehyde, dimethylacetal diethyl acetal, acrylamidoglycolic acid, methylacrylamidoglycolate methyl ether, isobutylmethylol acrylamide and the like. NMA and MAMD are the crosslinkers of choice and are the ones of commercial choice. Typically, these acids and self-crosslinking monomers are incorporated in an amount of from 0.2 to 10% by weight and preferably 0.5 to 5% by weight. Exemplary polymers for barrier applications have a vinyl acetate content of from 25 to 80%, the ethylene content from 20 to 75%, and the level of carboxylic acid or self-crosslinking monomer from 0 to 5% by weight of the polymer.

Other ethylenically unsaturated monomers can be employed for emulsion copolymerization with vinyl acetate-ethylene include, but are not limited to $C_1$ to $C_{15}$ alkyl vinyl ester, vinyl chloride, a $C_1$ to $C_{15}$ alkyl acrylate or a $C_1$ to $C_{15}$ alkyl methacrylate, such as methyl(meth)acrylate, ethyl (meth)acrylate, propyl(meth)acrylate, butyl(meth)acrylate, and 2-ethylhexyl(meth)acrylate, a $C_1$ to $C_6$ hydroxyalkyl (meth)acrylate, such as, hydroxyethyl(meth)acrylate and hydroxypropyl (meth)acrylate, a $C_1$ to $C_{15}$ alkyl maleate, $C_1$ to $C_{15}$ alkyl fumarate, acrylic acid, methacrylic acid, maleic anhydride, sodium vinyl sulfonate, 2-acrylamido-2-methyl propanesulfonate, and mixtures thereof; nitrogen containing mono-olefinically unsaturated monomers, particularly nitriles, and amides. The monomers can be incorporated in minor amounts, e.g., from 0 to about 10% by weight, preferably less than 5% by weight of the polymer.

It has been found that in the development of vinyl acetate-ethylene polymers for barrier applications by emulsion polymerization that the concentration of vinyl acetate and ethylene in the polymer is not solely responsible for its use as a barrier coating. It has been found that there needs to be a sufficient level of amorphous ethylene-vinyl acetate polymer segments to provide adhesion and flexibility to a substrate and a sufficient level of crystalline ethylene polymer segments to provide the proper balance of barrier characteristics and non-blocking. Polymerized ethylene segments lead to ethylene crystallinity in the polymer.

Crystalline polyethylene domains in the polymer impart a $T_m$ and $H_f$ to the polymer. It has also been found that by influencing the balance of amorphous ethylene-vinyl acetate domains and crystalline ethylene domains in the polymer, one can generate a range of aqueous copolymer dispersions where the polymer exhibits a $T_g$, $T_m$, $H_f$, and a high tensile storage modulus at high temperatures; i.e., temperatures of about 115° C.

In terms of crystalline segments, the polymers of this invention have a crystalline heat of fusion ranging from 5 to 100 joules per gram (J/g), preferably 10 to 70 J/g and a crystalline melting point ranging from 35 to 110° C., preferably 50 to 90° C.

Crystalline segments and the degree of branching in the polymer impart a high tensile storage modulus and are highly viscous with minimal flow properties at temperatures where other vinyl acetate-ethylene polymers melt and exhibit melt flow characteristics. The polymers described herein maintain a high viscosity and resistance to flow at temperatures well above their melt temperatures. The modulus should be at least $1 \times 10^5$ in dynes/cm$^2$ (preferably $2 \times 10^5$) at 115° C. as measured at a test frequency of 6.28 rad/sec. The $T_g$ of the polymer can be from about +25 to 40° C. A $T_g$ of −25 to −35° C. is preferred for use on creased or folded paper.

The $T_g$ of the polymer can be controlled by adjusting the ethylene content, i.e., generally the more ethylene present in the polymer relative to other comonomers, the lower the $T_g$. However, it has been found that under certain polymerization conditions where formation of crystalline polyethylene domains are favored, the $T_g$ does not continue to systematically decrease in proportion to the increase in ethylene concentration.

One preferred way to enhance crystalline domain formation of ethylene in the polymer is to delay or stage the addition of vinyl acetate during the polymerization process such that the unreacted vinyl acetate level present in the reactor is minimal at different stages during the process, i.e., below 5% unreacted free vinyl acetate monomer. Particularly, in the absence of carboxyl or self-crosslinking functionality, it is preferred to stage the addition of vinyl acetate in the polymerization process over an initial period of time. Typically, one completes the addition within 75% of the total polymerization period and generally within 3 hours or less. Thus, vinyl acetate/ethylene polymerization can take place in the one stage where most, but not all, of the ethylene will reside in amorphous regions, and the formation of the majority of crystalline ethylene domains can occur in another stage of the polymerization process.

Other factors leading to crystalline ethylene domains within the polymer is the pressure and temperature of polymerization. Although pressure is influential in achieving higher ethylene concentration levels in the polymer, it also is a factor in determining whether the amount of ethylene which is present is in amorphous regions or crystalline domains. Temperature, also is relevant in the formation of ethylene crystallinity. Lastly, the level of initiator is also a factor in developing copolymers for barrier applications.

In the preferred process for effecting polymerization and the formation of polymers for barrier applications, polymerization of ethylene, vinyl acetate, and, optionally, carboxylic acid is initiated by thermal initiators or by redox systems. A thermal initiator is typically used at temperatures of about 60° C. or higher, preferably about 70° C. or higher. Redox systems can be used over a wide range of temperatures, but are typically used at temperatures of about 60° C. or lower. The amount of initiator used in the process typically is substantially higher than used in prior processes for forming aqueous based vinyl acetate/ethylene dispersion polymers. Typically, the level of initiator is at least 0.5% and typically greater than 0.8% by weight of the total monomer charged. In addition, it is preferred that the initiator is added over the time of polymerization. It is believed that a high radical flux created by the higher levels of initiator facilitates ethylene incorporation during this low pressure polymerization process and leads to crystalline ethylene segments and a branched polymer architecture in the resulting copolymer and thus exhibits a higher tensile storage modulus at elevated temperatures, thermal melting point, and a heat of fusion. Thermal initiators are well known in the emulsion polymer art and include, for example, ammonium persulfate, sodium persulfate, and the like. Suitable redox systems are based upon sulfoxylates, and peroxides. Combinations of sodium formaldehyde sulfoxylate and peroxides such as t-butyl hydroperoxide (t-BHP) and hydrogen peroxide are representative.

The ethylene and, optionally other monomers, then are introduced under pressure of less than about 2000 psig (13,891 kPa), e.g., 1200 to 1800 psig (8375 to 12,512 kPa), and agitation, and the temperature increased to reaction temperature. Initiator, vinyl acetate, and emulsifier are staged or added incrementally over the reaction period, and the reaction mixture maintained at reaction temperature for a time required to produce the desired product.

In forming an emulsion polymerized polymer, a stabilizing system based upon protective colloids and surfactants can be employed. A protective colloid employed as a component of one of the suitable stabilizing system described herein is a cellulosic colloid. An example of a cellulosic protective colloid is hydroxyethyl cellulose. The protective colloid can be used in amounts of about 0.1 to 10 wt %, preferably 0.5 to 5 wt %, based on the total monomers. Polyvinyl alcohol can also be used in the formulation.

The surfactant or emulsifier can be used at a level of about 1 to 10 wt %, preferably 1.5 to 6 wt %, based on the total weight of monomers and can include any of the known and conventional surfactants and emulsifying agents, principally the nonionic, anionic, and cationic materials, heretofore employed in emulsion polymerization. Among the anionic surfactants found to provide good results are alkyl sulfates and ether sulfates, such as sodium lauryl sulfate, sodium octyl sulfate, sodium tridecyl sulfate, and sodium isodecyl sulfate, sulfonates, such as dodecylbenzene sulfonate, alpha-olefin sulfonates and sulfosuccinates, and phosphate esters, such as the various linear alcohol phosphate esters, branched alcohol phosphate esters, and alkylphenolphosphate esters.

Examples of suitable nonionic surfactants include the Igepal surfactants, which are members of a series of alkylphenoxy-poly(ethyleneoxy)ethanols having alkyl groups containing from about 7 to 18 carbon atoms, and having from about 4 to 100 ethyleneoxy units, such as the octylphenoxy poly(ethyleneoxy)ethanols, nonylphenoxy poly(ethyleneoxy)ethanols, and dodecylphenoxy poly(ethyleneoxy) ethanols. Others include fatty acid amides, fatty acid esters, glycerol esters, and their ethoxylates, ethylene oxide/propylene oxide block polymers, secondary alcohol ethoxylates, and tridecylalcohol ethoxylates. Examples of common cationic surfactants are dialkyl quaternaries, benzyl quaternaries, and their ethoxylates.

Average particle size distributions for the polymer particles of the emulsion polymers of this invention range from 0.05 microns to 5 microns, preferably 0.10 microns to 2 microns.

Ethylene levels in the polymers were determined by mass balance.

Tensile storage modulus as a function of temperature was measured at a test frequency of 6.28 rad/sec and expressed as dynes/cm$^2$. More specifically, dynamic mechanical testing of the polymer samples for measuring tensile storage modulus was accomplished using the following procedure. ASTM-D-4065-94 and ASTM-D-5026-94 were used as guidelines for this procedure. Each polymer emulsion was cast as a film and allowed to dry a minimum of several days at ambient conditions. The dry film thickness was typically in the range of 0.3 to 0.5 mm. For samples that did not film form adequately at room temperature, the polymers were compression molded at 100 to 150° C. The specimens used for testing were die cut from the film and were about 6.3 mm wide and 30 mm long. The specimens were tested on a Rheometrics Solid Analyzer (RSA II), from Rheometric Scientific, Inc., to obtain the tensile dynamic mechanical properties. Data were obtained every 6° C. over the −100 to 200° C. range using a fiber/film fixture and a deformation frequency of 6.28 rad/sec. To help ensure linear viscoelastic conditions, the applied strains were typically 0.05% in the glassy region and up to 1% in the rubbery region. A soak time of one minute was used at each temperature to ensure isothermal conditions. For each temperature, the RSA II calculated the tensile storage modulus (E'), tensile loss modulus (E"), and tangent delta (tan δ) based on the width, thickness and length of the sample.

$T_g$, $T_m$, and $H_f$ were determined via differential scanning calorimetry (DSC) using a TA Instruments Thermal Analyst 3100 with DSC 2010 module. Polymer samples were thoroughly dried prior to testing. Samples were held at 100° C. in the calorimeter for 5 minutes, cooled to −75° C., and then the scan acquired at a heating rate of 20° C. per minute up to a final temperature of 200° C. The $T_g$ corresponds to the extrapolated onset values obtained from the baseline shift at the glass transition during the heating scan. The melting point temperature corresponds to the peak in the heat flow curve. The heat of fusion was calculated by integrating the area under the melting endotherm; the baseline for this integration was constructed by extrapolating the linear region of the heat flow curve after the melt, back to the point of intersection with the heat flow curve before the melt.

The polymeric barrier coating of this invention is designed to be used with many cellulosic products requiring barrier properties and these include paper, paperboard, bagstock, ticket stock, linerboard, bleached or natural Kraft, cardboard, or other box making materials. Other cellulosic products include cotton or cotton blends, wallpaper and wood products. The cellulosic products may be sized or pigmented as conventionally practiced.

The polymer emulsions can be directly coated onto cellulosic products such as paper and paperboard stock to afford a coated paper or paperboard that is resistance to oil, grease, solvent, and moisture vapor, thus eliminating additional production steps, such as polymer extrusion/lamination, and eliminating environmentally harmful substances, such as fluorochemicals. The dispersion can be applied close to the dry end of the paper machine just before the last drier.

The invention will be further clarified by a consideration of the following examples, which are intended to be purely exemplary of the invention.

EXAMPLE 1

Vinyl Acetate/Ethylene/Acrylic Acid Polymer Containing 63% Ethylene

An ethylene-vinyl acetate emulsion polymer containing crystalline ethylene segments was prepared by the following procedure: A three-gallon stainless steel pressure reactor was charged with the following mixture:

| Material | Mass charged, g |
| --- | --- |
| DI Water | 2400 |
| Rodapon UB sodium lauryl sulfate | 165 |

-continued

| Material | Mass charged, g |
|---|---|
| Natrosol 250GR protective colloid | 1500 |
| Vinyl Acetate | 60 |

Rhodapon UB sodium lauryl sulfate (30% aqueous solution); supplied by Rhodia
Natrosol 250GR (2% aqueous solution); hydroxyethyl cellulose, supplied by Rhodia.

The following delay mixtures were utilized:

| Material | Mass charged, g |
|---|---|
| Aqueous 10.0% ammonium persulfate containing 3.5% sodium bicarbonate | 315 |
| Aqueous 10.0% sodium lauryl sulfate | 750 |
| 90:10 Vinyl Acetate/Acrylic acid mixture | 1464 |
| Ethylene | 1800 psig for 7 hours |

Agitation at 100 rpm was begun with a nitrogen purge. Agitation was then increased to 600 rpm and the reactor heated to 80° C. After pressurizing the reactor with ethylene to 1800 psig (12,512 kPa), 15 g of initiator solution was added at a rate of 10.0 g/min. At the 10 minute mark, the monomer delay was begun at 3.49 g/min, the surfactant delay was begun at 1.79 g/min, and the initiator delay was re-started at 0.71 g/min. Ethylene pressure of 1800 psig (12,512 kPa) was maintained for 420 minutes. The vinyl acetate delay, surfactant delay, initiator delay, and ethylene supply were completed at the 420 minute mark, followed by holding the reaction mixture at temperature for another 30 minutes. The reaction was then cooled to 30° C., transferred to a degasser, and 6 g of Rhodaline 675 defoamer was added. The following properties of the resulting emulsion copolymer were measured:

| Copolymer Composition (by solids calculation) | 63% Ethylene<br>33.5% Vinyl acetate<br>3.5% Acrylic acid |
|---|---|
| $T_g$ Midpoint (° C.) | −32.3 |
| Viscosity (60/12 rpm) (cps) | 3500/6500 |
| % solids | 46.8 |
| pH | 4.45 |
| $T_m$ (° C.)/Heat of Fusion (J/g) | 68.4/26.8 |

EXAMPLE 2

Vinyl Acetate/Ethylene/Acrylic Acid Polymer Containing 51% Ethylene

An emulsion polymer containing crystalline ethylene segments was prepared by the following procedure: A one-gallon stainless steel pressure reactor was charged with the following mixture:

| Material | Mass charged, g |
|---|---|
| DI Water | 1100 |
| Aerosol MA80I | 10 |
| 95:5 Vinyl Acetate/Acrylic acid mixture | 120 |

Aerosol MA80I supplied by Cytec

The following delay mixtures were utilized:

| Material | Mass charged, g |
|---|---|
| Aqueous 10.0% ammonium persulfate containing 3.5% sodium bicarbonate | 131 |
| Rhodacal DS-10, diluted to 15% active | 260 |
| 95:5 Vinyl Acetate/Acrylic acid mixture | 540 |
| Ethylene | 1400 psig for 5.5 hours |

Rhodacal DS-10 supplied by Rhodia

Agitation at 100 rpm was begun with a nitrogen purge. Agitation was then increased to 900 rpm and the reactor heated to 80° C. After pressurizing the reactor with ethylene to 1400 psig (9754 kPa), 15 g of initiator solution was added at a rate of 5.0 g/min. When the 15 g of initiator had been added, the initiator delay rate was reduced to 0.30 g/min. At the 15 minute mark, the monomer delay was begun at 3.0 g/min and the surfactant delay was begun at 0.72 g/min. Ethylene pressure of 1400 psig was maintained for 330 minutes. The vinyl acetate delay was stopped at the 3 hour mark. The surfactant delay and ethylene supply were stopped at the 330 minute mark. The initiator delay was stopped at the 360 minute mark, followed by holding the reaction mixture at temperature for another 30 minutes. The reaction was then cooled to 30° C., transferred to a degasser, and 2 g of Rhodaline 675 defoamer was added. The following properties of the resulting emulsion copolymer were measured:

| Copolymer Composition (by solids calculation) | 51% Ethylene<br>46.5% Vinyl acetate<br>2.5% Acrylic acid |
|---|---|
| $T_g$ Midpoint (° C.) | −29.9 |
| Viscosity (60/12 rpm) (cps) | 400/1260 |
| % solids | 49.1 |
| pH | 4.53 |
| $T_m$ (° C.)/Heat of Fusion (J/g) | 86.7/23.6 |

EXAMPLE 3

Vinyl Acetate/Ethylene/Acrylic Acid Polymer Containing 41% Ethylene

An emulsion polymer containing crystalline ethylene segments was prepared by the following procedure: A one-gallon stainless steel pressure reactor was charged with the following mixture:

| Material | Mass charged, g |
|---|---|
| DI Water | 700 |
| Rhodacal DS-10 | 9 |
| Natrosol 250GR protective colloid (2% solution) | 500 |
| Ferrous ammonium sulfate (2% solution in water) | 6 |
| 95:5 Vinyl Acetate/Acrylic Acid mixture | 120 |

The following delay mixtures were utilized:

| Material | Mass charged, g |
| --- | --- |
| Aqueous 4.0% t-BHP | 133 |
| Aqueous 8% sodium formaldehyde sulfoxylate | 133 |
| Rhodacal DS-10 diluted to 15% active solution | 306 |
| 95:5 vinyl acetate/acrylic acid solution | 540 |
| Ethylene | 1400 psig for 5.5 hours |

Agitation at 100 rpm was begun with a nitrogen purge. Agitation was then increased to 900 rpm and the reactor heated to 60° C. The reactor was then pressurized with ethylene to 1400 psig (9754 kPa). 10 g of sodium formaldehyde sulfoxylate solution was then added. Delay feeds of tert-butylhydrogen peroxide at 0.3 g/min and sodium formaldehyde sulfoxylate at 0.3 g/min were begun. After 10 minutes, the monomer delay was begun at 3.0 g/min, the surfactant delay was begun at 0.85 g/min, and the redox delays were reduced to 0.20 g/min. Ethylene pressure of 1400 psig was maintained for 330 minutes. The monomer delay was stopped at the 3 hour mark. Ethylene supply was stopped at the 330 minute mark. The surfactant delay and redox delays were stopped at the 360 minute mark. Next, the reaction was cooled to 30° C. and transferred to a degasser, and 2 g of Rhodaline 675 defoamer was added. The following properties of the resulting emulsion copolymer were measured:

| | |
| --- | --- |
| Copolymer Composition (by solids calculation) | 41% Ethylene<br>56% Vinyl acetate<br>3% Acrylic Acid |
| $T_g$ Midpoint (° C.) | −27.4 |
| Viscosity (60/12 rpm) (cps) | 700/1500 |
| % solids | 41 |
| pH | 4.15 |
| $T_m$ (° C.)/Heat of Fusion (J/g) | 91.2/25.7 |

EXAMPLE 4

Vinyl Acetate/Ethylene/Acrylic Acid Polymer Containing 74% Ethylene

An emulsion polymer containing crystalline ethylene segments was prepared by the following procedure: A three-gallon stainless steel pressure reactor was charged with the following mixture:

| Material | Mass charged, g |
| --- | --- |
| DI Water | 3000 |
| Rodapon UB sodium lauryl sulfate | 180 |
| Natrosol 250GR protective colloid | 1500 |
| Vinyl Acetate solution containing 1.25 wt % Acrylic acid | 300 |

The following delay mixtures were utilized:

| Material | Mass charged, g |
| --- | --- |
| Aqueous 10.0% ammonium persulfate containing 3.0% sodium bicarbonate | 363 |
| Aqueous 10.0% sodium lauryl sulfate | 990 |
| Vinyl Acetate solution containing 1.25 wt % Acrylic acid | 750 |
| Ethylene | 1400 psig for 5 hours |

Agitation at 100 rpm was begun with a nitrogen purge. Agitation was then increased to 600 rpm and the reactor heated to 80° C. After pressurizing the reactor with ethylene to 1400 psig (9754 kPa), 15 g of initiator solution was added at a rate of 5.0 g/min. The initiator rate was then reduced to 0.90 g/min. At the 10 minute mark, the monomer delay was begun at 8.33 g/min and the surfactant delay was begun at 3.30 g/min. Ethylene pressure of 1400 psig was maintained for 300 minutes. The vinyl acetate delay was stopped at the 90 minute mark. At the 2 hour mark the initiator rate was increased to 1.30 g/min. The surfactant delay, initiator delay, and ethylene supply were stopped at the 300 minute mark, followed by holding the reaction mixture at temperature for another 30 minutes. The reaction was then cooled to 30° C., transferred to a degasser, and 2 g of Rhodaline 675 defoamer was added. The following properties of the resulting emulsion copolymer were measured:

| | |
| --- | --- |
| Copolymer Composition (by solids calculation) | 74% Ethylene<br>25.7% Vinyl acetate<br>0.3% Acrylic acid |
| $T_g$ Midpoint (° C.) | −33.4 |
| Viscosity (60/12 rpm) (cps) | 200/300 |
| % solids | 41.4 |
| pH | 6.0 |
| $T_m$ (° C.)/Heat of Fusion (J/g) | 95.0/51.6 |

EXAMPLE 5

Vinyl Acetate/Ethylene/Acrylic Acid Polymer Containing 52% Ethylene

A one-gallon stainless steel pressure reactor was charged with the following mixture:

| Material | Mass charged, g |
| --- | --- |
| DI Water | 700 |
| Rodapon UB sodium lauryl sulfate | 50 |
| Natrosol 250GR HEC | 500 |
| Ferrous ammonium sulfate (2% solution in water) | 6 |
| Vinyl Acetate | 200 |

The following delay mixtures were utilized:

| Material | Mass charged, g |
| --- | --- |
| Aqueous 4.0% t-BHP | 101 |
| Aqueous 8% sodium formaldehyde sulfoxylate | 103 |
| Aqueous 15.0% sodium lauryl sulfate | 195 |

-continued

| Material | Mass charged, g |
|---|---|
| 87.5% vinyl acetate and 12.5% acrylic acid solution | 250 |
| Ethylene | 1600 psig for 5 hours |

Agitation at 100 rpm was begun with a nitrogen purge. Agitation was then increased to 800 rpm and the reactor heated to 60° C. Ten grams of sodium formaldehyde sulfoxylate solution was then added. Delay feeds of tert-butylhydrogen peroxide at 0.3 g/min and sodium formaldehyde sulfoxylate at 0.3 g/min were begun. After most of the initial charge of vinyl acetate was consumed, the reactor was pressurized with ethylene to 1600 psig (11,133 kPa). Then the monomer delay was begun at 0.83 g/min and the surfactant delay was begun at 0.65 g/min. Ethylene pressure of 1600 psig was maintained for 5 hours. The monomer delay, surfactant delay, and ethylene pressure were completed at the 5 hour mark. The redox initiator delay feeds were completed at the 320 minute mark. Next, the reaction was cooled to 35° C. and transferred to a degasser, and 2 g of Rhodaline 675 defoamer was added. The following properties of the resulting emulsion polymer were measured:

| | |
|---|---|
| Polymer Composition (by solids calculation) | 52% Ethylene<br>44.6% Vinyl acetate<br>3.4% Acrylic Acid |
| $T_g$ Onset (° C.) | −31.5 |
| Viscosity (60/12 rpm) (cps) | 1490/3870 |
| 100/325 mesh grit (ppm) | <170/<200 |
| % solids | 38.6 |
| pH | 4.3 |
| $T_m$ (° C.)/$H_f$ (J/g) | 71.7/46.1 |

EXAMPLE 6

Vinyl Acetate/Ethylene/Acrylic Acid Polymer Containing 45% Ethylene

A polymer emulsion containing crystalline ethylene segments was prepared by first charging a one-gallon stainless steel pressure reactor with the following mixture:

| Material | Mass charged, g |
|---|---|
| DI Water | 700 |
| Rhodacal DS-10 | 9 |
| Natrosol 250GR (2% aqueous solution) | 500 |
| Ferrous ammonium sulfate (2% aqueous solution) | 6 |
| Monomer Solution comprising 95.0 wt % vinyl acetate, 4.7 wt % acrylic acid, and 0.3 wt % dodecylmercaptan | 120 |

The following delay mixtures were utilized:

| Material | Mass charged, g |
|---|---|
| Aqueous 4.0% t-BHP | 128 |
| Aqueous 8% sodium formaldehyde sulfoxylate | 140 |

-continued

| Material | Mass charged, g |
|---|---|
| Aqueous solution containing 52.5 g Rhodacal DS-10 and 297.5 g water | 306 |
| Monomer Solution comprising 95.0 wt % vinyl acetate, 4.7 wt % acrylic acid, and 0.30 wt % dodecylmercaptan | 540 |
| Ethylene | 1400 psig for 5.5 hours |

Agitation at 100 rpm was begun with a nitrogen purge. Agitation was then increased to 900 rpm and the reactor heated to 60° C. After pressurizing the reactor with ethylene to 1400 psig (9754 kPa), 10 g of 8% aqueous sodium formaldehyde sulfoxylate was added to the reactor. Delay feeds of tert-butylhydrogen peroxide (4%) at 0.4 g/min. and 8% sodium formaldehyde sulfoxylate at 0.4 g/min were begun. After a 10 minute period, the surfactant delay was begun at 0.85 g/min and the monomer solution delay was begun at 3.0 g/min. Redox rates were adjusted during the reaction period to maintain reasonable reaction rates. Ethylene pressure of 1400 psig was maintained for 5.5 hours. The monomer solution delay was turned off at the 3 hour mark. The ethylene makeup valve was closed at the 5.5 hour mark. The surfactant delay and initiator delay were stopped at the 6 hour mark. The reaction was then cooled to 35° C., transferred to a degasser to remove unreacted ethylene, and 2 g of Rhodaline 675 defoamer was added. The following properties of the resulting emulsion polymer were measured:

| | |
|---|---|
| Polymer Composition (By solids calculation) | 45% Ethylene<br>52.4% Vinyl acetate<br>2.6% Acrylic Acid |
| $T_g$ Onset (° C.) | −27.1 |
| Viscosity (60/12 rpm) (cps) | 710/1520 |
| 100/325 mesh coagulum (ppm) | <150/<69 |
| % solids | 42.8 |
| pH | 4.4 |
| $T_m$ (° C.)/Heat of Fusion (J/g) | 93.0/21.0 |

EXAMPLE 7

Vinyl Acetate/Ethylene/N-Methylol Acrylamide Polymer Containing 63% Ethylene

A three-gallon stainless steel pressure reactor was charged with the following mixture:

| Material | Mass charged, g |
|---|---|
| DI Water | 3300 |
| Aerosol MA-80I | 30 |
| Vinyl Acetate | 360 |

Aerosol MA-80I supplied by Rhodia

The following delay mixtures were utilized:

| Material | Mass charged, g |
|---|---|
| Aqueous 10.0% ammonium persulfate containing 4.0% sodium bicarbonate | 345 |

-continued

| Material | Mass charged, g |
|---|---|
| Aqueous 15.0% diluted solution of Rhodacal DS-10 | 795 |
| Vinyl Acetate | 1655 |
| N-methylolacrylamide (48%) (NMA) | 419 |
| Ethylene | 1400 psig for 5.5 hours |

Agitation at 100 rpm was begun with a nitrogen purge. Agitation was then increased to 600 rpm and the reactor heated to 80° C. After pressurizing the reactor with ethylene to 1400 psig (9754 kPa), 15 g of initiator solution was added at a rate of 5.0 g/min. After the 15 g of initiator were in the reactor, the initiator delay rate was reduced to 0.90 g/min. At initiation, the vinyl acetate delay was begun at 9.0 g/min, the surfactant delay was begun at 2.16 g/min, and the NMA delay was begun at 1.17 g/min. Ethylene pressure of 1400 psig was maintained for 5.5 hours. The vinyl acetate delay was stopped at the 3 hour mark. The ethylene supply was stopped at the 5.5 hour mark. The surfactant delay, NMA delay, and initiator delay were stopped at the 6 hour mark, followed by holding the reaction mixture at temperature for another 30 minutes. The reaction was then cooled, transferred to a degasser, and 2 g of Rhodaline 675 defoamer was added. The following properties of the resulting emulsion polymer were measured:

| Polymer Composition (by solids calculation) | 43% Ethylene<br>52% Vinyl acetate<br>5% NMA |
|---|---|
| $T_g$ Onset (° C.) | −29.6 |
| Viscosity (60/12 rpm) (cps) | 53/55 |
| 100/325 mesh coagulum (ppm) | <35/<236 |
| % solids | 47.2 |
| pH | 5.2 |
| $T_m$ (° C.)/Heat of Fusion (J/g) | 79.0/12.2 |

EXAMPLE 8

Vinyl Acetate/Ethylene/Acrylic Acid Polymer Containing 49% Ethylene

The procedure of Example 2 was followed, except the initial reactor charge consisted of 300 g of Natrosol 250 GR (2%), 10 g of Aerosol MA801, 800 g of water, and 120 g of the monomer solution.

| Polymer Composition (by solids calculation) | 49% Ethylene<br>48.5% Vinyl acetate<br>2.5% acrylic acid |
|---|---|
| $T_g$ Onset (° C.) | −29.2 |
| Viscosity (60/12 rpm) (cps) | 3200/7200 |
| 100/325 mesh coagulum (ppm) | <225/<218 |
| % solids | 48.7 |

-continued

| Polymer Composition (by solids calculation) | 49% Ethylene<br>48.5% Vinyl acetate<br>2.5% acrylic acid |
|---|---|
| pH | 4.5 |
| $T_m$ (° C.)/Heat of Fusion (J/g) | 87.1/15.0 |

EXAMPLE 9

Comparative Test Performance of Polymeric Compositions For Barrier Applications

Samples from Examples 1-8 emulsion polymers were coated onto 11 point solid bleached sulfate (SBS) board (basis weight of 120 pounds/3000 sq.ft.) with a wire round rod. Dry coat weight of approximately 1.5 pounds/3000 sq. ft. was achieved with a #10 rod. Wet coatings were dried for 90 seconds at 250° F. Performance results were tabulated and are shown below along with the results for several commercially available emulsion polymers. The first commercial sample is a commercial greaseproof paper, which is treated with a fluorochemical to provide resistance to grease and oils for applications such as popcorn bags, pet food bag, and fast food packaging. The second commercial sample is of a paper/polyethylene composite more commonly known as a poly-coated board sample for applications such as frozen food and aseptic packaging. The sample is made by extrusion coating 0.5 mils of low-density polyethylene (LDPE) onto 16 point SBS board.

Coated sheets were placed in a constant temperature and humidity room and conditioned per TAPPI method T 402 om-93, prior to testing under the same procedure.

Corn oil resistance of the coated sheets to penetration of oil was accomplished with a corn oil holdout test. Two drops of corn oil (Mazola) were placed on the coated surface of each sample. Samples were examined each hour, over 24 hours, for visual discoloration of the basesheet, which would indicate that the oil had penetrated the coating.

Grease and oil resistance of the coating was evaluated per TAPPI method T 559 pm-96, also known as the kit test.

Kit testing was accomplished on the flat-coated samples (as coated) and on samples, which were folded once in the machine direction and then in the cross-machine direction. Folded samples were tested in the cross (+) area. The ability of the coated sheets to absorb water was evaluated via the Cobb water absorption test (T 441 om-90).

Turpentine resistance and determination of coating defects was accomplished with TAPPI method T 454 om-94.

Moisture vapor transmission rate were measured on the coated samples according to TAPPI method T 464 om-95.

Blocking (coated side to uncoated side) was assessed using TAPPI UM 565 at 44% and 75% relative humidity.

Hot Vegetable Oil Test: To simulate packaging environments for hot, high fat/oil content foods, a drop of vegetable oil or olive oil was placed onto the coated paper at elevated temperature. The amount of time for the hot oil to penetrate through to the backside of the paper sample was recorded. Timing was stopped at 180 to 200 seconds. The coating must inhibit hot oil penetration for a minimum of 180 to 200+ seconds in order to be acceptable.

| | Corn Oil Holdout (Time) | Kit Rating Flat/ Folded | Turpentine Holdout Flat/Folded (min) | Cobb Water Absorption (g/m$^2$) | Hot Vegetable Oil Test (sec) | Blocking 44% RH Coat/ Uncoat | Blocking 75% RH Coat/ Uncoat |
|---|---|---|---|---|---|---|---|
| Commercial Greaseproof Paper (Fluorochemically Treated) | 24 hr+ | 12/9 | 30+/30+ | 20 | ND | None | None |
| Commercial Polycoated Board (0.5 mil LDPE/16 pt SBS board) | 24 hr+ | 12/1 | 30+/<1 | 0 | 180+ | None | None |
| Basepaper (120 lbs/3000 sq ft SBS board) | 4 min | 1/1 | <1 | 31 | 5 | — | — |
| Example 1 | 24 hr+ | 12/10 | 30+/30+ | 4 | 180+ | SI. Tack | None |
| Example 2 | 24 hr+ | 12/9 | 30+/30+ | 12 | 180+ | None | None |
| Example 3 | 24 hr+ | 12/12 | 30+/30+ | 16 | 180+ | None | None |
| Example 4 | 24 hr+ | 12/7 | 30+/6 | 3 | 180+ | None | None |
| Example 5 | 24 hr+ | 12/6 | 30+/4 | 4 | 180+ | None | None |
| Example 6 | 24 hr+ | 12/11 | 30+/30+ | 23.2 | 180+ | None | None |
| Example 7 | 24 hr+ | 12/10 | 30+/30+ | 8 | 180+ | None | None |
| Example 8 | 24 hr+ | 12/8 | 30+/20 | ND | 180+ | None | None |
| Poly(vinyl acetate) homopolymer/$T_g$ = 33° C. | <23 hr | 7/4 | 30+/<1 | 2.4 | 10 | SI. Tack | SI. Tack |
| Airflex 100HS VAE polymer/$T_g$ = 7° C. | <23 hr | 8/6 | 30+/<1 | 4.0 | 20 | SI. Tack | SI. Tack |
| Commercial VAE polymer/$T_g$ = 17° C. | 24 hr+ | 9/9 | 30+/<1 | 20.8 | 5 | None | SI. Tack |
| Commercial Self Crosslinking VAE*/$T_g$ = 10° C. | 24 hr+ | 10/5 | 20/4 | 24.8 | 45 | None | None |
| Commercial VAE-acrylic acid polymer/$T_g$ = −20° C. | 24 hr+ | 12/9 | 30+/<1 | 15.2 | 180+ | Blocked | Blocked |
| Commercial VAE-acrylic acid polymer/$T_g$ = −40° C. | 24 hr+ | 12/11 | 30+/30+ | 6.8 | 20 | Blocked | Blocked |

*VAE-N-methylolacrylamide copolymer

All paper samples coated with the emulsion polymers described in the above examples show corn oil holdout, kit test performance, and turpentine holdout results comparable to the fluorochemically treated greaseproof paper. The emulsion polymers of this invention vis-à-vis fluorochemically treated paper also reduce the ability of the paper to absorb water significantly, which is a benefit for many applications.

The emulsion polymers also showed performance comparable to the commercial polycoated board. One advantage of the emulsion polymers of this invention is that they are significantly more repulpable than extruded LDPE allowing for fiber recovery. In addition, the emulsion polymers of this invention can be applied in the paper making process thereby saving a processing step compared to LDPE extrusion.

The emulsion polymers of Examples of 1-8 showed better kit performance (both flat and folded) than the commercially available poly(vinyl acetate) (PVAc) and many of the poly(vinyl acetate-ethylene) (VAE) polymers. Corn oil and turpentine results were comparable.

The emulsion polymers of this invention also showed better blocking resistance than the commercial VAE, including those incorporating acrylic acid, and the PVAc polymers. This was somewhat unexpected since the emulsion polymers of this invention are low in $T_g$ and contain significantly more ethylene than the commercial polymers.

There was a major difference in hot vegetable/olive oil resistance between the polymers of this invention and the commercial polymers which do not have sufficient crystallinity to demonstrate a thermal melt temperature and heat of fusion. Polymers of Example 1-8 exhibit superior hot vegetable/olive oil resistance by preventing hot oil penetration into the cellulosic substrate in excess of 180+ seconds. The one commercial VAE-acrylic acid ($T_g$=−20° C.) polymer that had good resistance to hot oil penetration also had poor blocking resistance.

What is claimed is:

1. In a cellulosic product in contact with a material containing moisture, an oil, grease, solvent or fat comprised of a cellulosic substrate having a polymer coating applied thereto which imparts a barrier against said moisture, oil, grease, solvent or fat contained in said material when in contact therewith, the improvement which comprises:

said polymer coating comprising an ethylene-vinyl acetate polymer comprised of crystalline ethylene segments prepared by aqueous emulsion polymerization of ethylene and vinyl acetate in the presence of a stabilizing system consisting essentially of a surfactant or a protective colloid in combination with a surfactant, said ethylene-vinyl acetate polymer having:

(a) a crystalline melting point ranging from 35 to 110° C. measured at a heat rate of 20° C. per minute; and, (b) a tensile storage modulus of at least 1×10$^5$ dynes/cm$^2$ at a temperature of 115° C. and measured at 6.28 rad/sec.

2. The cellulosic product of claim 1 wherein the polymer is comprised of from 15 to 90% by weight of polymerized units of vinyl acetate and from about 10 to 85% by weight of polymerized units of ethylene based upon the total weight of the polymer.

3. The cellulosic product of claim 2 wherein the polymer is comprised of from 25 to 80% by weight of polymerized units of vinyl acetate and from about 20 to 75% by weight of polymerized units of ethylene based upon the total weight of the polymer.

4. The cellulosic product of claim 2 wherein the polymer is comprised of from 35 to 75% by weight of polymerized units of vinyl acetate and from about 25 to 65% by weight of polymerized units of ethylene based upon the total weight of the polymer.

5. The cellulosic product of claim 4 wherein the polymer is comprised of from 30 to 50% by weight of polymerized units of vinyl acetate and from about 50 to 70% by weight of polymerized units of ethylene based upon the total weight of the polymer.

6. The cellulosic product of claim 2 wherein polymerized units of a carboxylic acid or N-methylol acrylamide are present in said polymer in an amount from about 0.2 to about 10% by weight of said polymer.

7. The cellulosic product of claim 3 wherein said polymer has a tensile storage modulus of at least 2×10$^5$ dynes/cm$^2$ at 115° C. measured at 6.28 rad/sec.

8. The cellulosic product of claim 7 wherein the polymer consists essentially of polymerized units of ethylene, vinyl acetate, and acrylic acid.

9. The cellulosic product of claim 8 wherein the crystalline heat of fusion of said polymer is from about 5 to 100 joules per gram as measured at a heat rate of 20° C. per minute.

10. The cellulosic product of claim 9 wherein the glass transition temperature is from +25° C. to about −40° C. as measured at a heat rate of 20° C. per minute.

11. The cellulosic product of claim 10 wherein crystalline thermal melting point ranges from 50 to 90° C. as measured at a heat rate of 20° C. per minute.

12. The cellulosic product of claim 8 wherein the $T_g$ of the polymer is from −25 to −35° C.

13. The cellulosic product of claim 12 wherein the crystalline heat of fusion ranges from preferably 15 to 70 joules per gram as measured at a heat rate of 20° C. per minute.

14. In a paper or paperboard product in contact with a food product and comprised of a paper or paperboard substrate having a polymer coating applied thereto which imparts a barrier to moisture, oil or fat contained in food product, the improvement which comprises:

said polymer coating comprising a polymer consisting essentially of polymerized units of ethylene, vinyl acetate, and carboxylic acid or N-methylol acrylamide, said polymer prepared by aqueous emulsion polymerization of ethylene, vinyl acetate and carboxylic acid or N-methylol acrylamide in the presence of a stabilizing system consisting essentially of a surfactant or a protective colloid in combination with a surfactant, said ethylene-vinyl acetate polymer having:

(a) a crystalline melting point ranging from 50 to 90° C. measured at a heat rate of 20° C. per minute; and, (b) a tensile storage modulus of at least $1 \times 10^5$ dynes/cm$^2$ at a temperature of 115° C. and measured at 6.28 rad/sec.

15. The paper or paperboard product of claim 14 wherein the $T_g$ of the polymer ranges from −25 to −35° C.

16. The paper or paperboard product of claim 15 wherein the heat of fusion of said polymer is from 10 to 70 joules per gram as measured at a heat rate of 20° C. per minute.

17. The paper or paperboard product of claim 16 wherein the ethylene is present in an amount from 35 to 75 weight percent vinyl acetate, 25 to 65 weight percent ethylene, and from 0.2 to 10 percent by weight carboxylic acid or N-methylol acrylamide.

18. The paper or paperboard product of claim 16 wherein the polymer consists essentially of ethylene, vinyl acetate, and acrylic acid.

* * * * *